(12) United States Patent
Kinast (10) Patent No.: US 7,257,438 B2
(45) Date of Patent: Aug. 14, 2007

(54) PATIENT-WORN MEDICAL MONITORING DEVICE

(75) Inventor: Eric Kinast, Santa Ana, CA (US)

(73) Assignee: Datascope Investment Corp., Montvale, NJ (US)

(*) Notice: Subject to any disclaimer, the term of this patent is extended or adjusted under 35 U.S.C. 154(b) by 388 days.

(21) Appl. No.: 10/341,833

(22) Filed: Jan. 14, 2003

(65) Prior Publication Data

US 2004/0019288 A1    Jan. 29, 2004

Related U.S. Application Data

(63) Continuation-in-part of application No. 10/201,075, filed on Jul. 23, 2002, now abandoned.

(51) Int. Cl.
*A61B 5/00* (2006.01)
(52) U.S. Cl. .................. 600/509; 600/301; 600/386
(58) Field of Classification Search ................ 600/301, 600/386, 509
See application file for complete search history.

(56) References Cited

U.S. PATENT DOCUMENTS

| | | | | |
|---|---|---|---|---|
| 4,635,646 A | * | 1/1987 | Gilles et al. | 600/509 |
| 4,662,378 A | * | 5/1987 | Thomis | 600/382 |
| 5,027,824 A | * | 7/1991 | Dougherty et al. | 600/515 |
| 6,049,730 A | * | 4/2000 | Kristbjarnarson | 600/509 |
| 2003/0004403 A1 | * | 1/2003 | Drinan et al. | 600/301 |
| 2004/0077937 A1 | * | 4/2004 | Yarden | 600/386 |

* cited by examiner

*Primary Examiner*—Robert Pezzuto
*Assistant Examiner*—Yun Haeng Lee
(74) *Attorney, Agent, or Firm*—Lerner, David, Littenberg, Krumholz & Mentlik, LLP (57) ABSTRACT

A medical monitor includes a lanyard and an electronic package supported in the manner of a pendant. The lanyard includes integral electrodes or other sensors for making physiological measurements, auxiliary components and connectors for electrically connecting the electrodes or sensors to the electronic package. The physiological measurements may be stored in the monitor for later readout, or may be transmitted, before or after processing, to a remote location.

34 Claims, 7 Drawing Sheets

FIG. 1

PRIOR ART

FIG. 2

PRIOR ART

PATIENT-WORN MEDICAL MONITORING DEVICE

RELATED APPLICATIONS

This applications is a continuation-in-Part of U.S. patent application Ser. No. 10/201075, filed on Jul. 23, 2002, herein incorporated by reference in its entirety, and claims the benefit of Provisional Application No. 60/308,070 filed on Jul. 26, 2001.

BACKGROUND OF THE INVENTION

1. Field of the Invention

The invention relates to a medical monitoring device. More particularly, the invention relates to a patient-worn electronic monitoring device.

2. Description of the Prior Art

Modern medical practice makes extensive use of electronic vital signs monitoring. As technology has progressed, electronic monitoring devices have become more compact, easier to use, and have been made available to larger segments of the patient population. Today, most electronic monitors are what are termed "bedside monitors." A bedside monitor consists of an electronics and display unit placed in close proximity to a patient bed. Cables connect the monitor to various sensors attached to the patient. While such arrangements have become highly developed, and permit comprehensive monitoring of the patient, the disadvantages are obvious. A patient can only be monitored when confined to bed, or otherwise restricted to the immediate vicinity of the monitor, as dictated by the connecting cables.

Portable or transportable monitors have been developed to allow the patient to be moved within the hospital, or even between healthcare facilities. Such monitors are quite similar to traditional bedside monitors, but are made somewhat smaller and lighter in weight, and have provision to operate for some time from internal battery power. But such devices remain sufficiently heavy and bulky that they require special attention to move along with the patient. Often, the monitor is provided with a bracket or other arrangement allowing it to be attached to the wheeled bed occupied by the patient during transport. While such an arrangement makes it possible to relocate a patient while continuing monitoring, it does not permit normal ambulation of the patient.

In many cases, patients are sufficiently able-bodied that they may ambulate normally, and are not confined to bed, yet it is desired to continuously monitor their condition. Indeed, in some cases ambulation of the patient is a necessary part of medical care, as in the case of a heart patient where the exertion associated with walking and other normal activity may be necessary to reveal an underlying heart condition. To serve these cases, patient-worn monitoring devices have been developed. Often, such devices are limited to monitoring a single vital sign. As the heart may be considered the most vital organ, the usual parameter to be monitored is the electrocardiogram, or ECG.

Patient-wearable devices used to monitor a patient's ECG take two general forms. One form of device, often known as a holter monitor, simply records the patient's ECG signal for later analysis. The particular advantage of this sort of device is that monitoring can take place at any location, while the patient is going about normal daily activities. However, an obvious disadvantage is that there is no immediate indication of a deterioration in the patient's condition. Therefore, an alternate device, known as a telemetry monitor, has been developed. Such a device acquires the patient's ECG signal, and transmits it by radio link to a central monitoring and display location, where the ECG signal can be observed by clinical personnel and automated analysis systems. Any change in the patient's condition requiring clinical intervention is therefore immediately apparent and medical assistance can be dispatched to the patient. The disadvantage of telemetry systems is that they are operable only within premises where suitable receiving equipment is provided.

Current ambulatory ECG monitors found in clinical applications use electrodes of a type and configuration based on bedside monitor practice. Generally three to five adhesive electrodes are attached to the body in locations disposed on the chest. These electrodes are connected by leadwires or a cable to the monitor electronics. The monitor electronics is arranged in a wearable housing, generally supported by means of a pouch, sling, or belt clip. This arrangement is somewhat inconvenient, due to the presence of the leadwires and the bulk, weight, and method of support of the monitor electronics. Further, some skill is necessary to properly attach the electrodes, connect the leadwires and set the monitor in action. As such, monitoring devices of this type are only used in such clinical cases where the inconvenience and cost of the skilled application are justified.

Electrocardiogram devices using conventional electrode configurations can yield considerable information about the condition of the heart by skilled interpretation of the ECG waveforms produced. However, in many cases, even in clinical practice, such interpretation is not performed, and the monitor is used only to measure the patient's heart rate. This is always the case in certain non-clinical ECG applications, such as when the ECG signal is used to determine the pulse rate during exercise. In this case, conventional placement of electrodes can be abandoned, in favor of electrode configurations which facilitate convenient application of the monitoring device. Exercise ECG monitors are often configured as a small electronics housing secured by a belt tightened around the wearer's chest. The housing contains a pair of electrodes which contact the chest and acquire an ECG signal. The electronics trigger on each heartbeat and transmit a signal to a nearby readout device. The readout device counts the trigger signals within a unit time and displays the pulse rate.

While such exercise monitors are far simpler to apply and lack the objectionable leadwires and separate electronics box of clinical ambulatory monitors, they do not answer fully to clinical purposes, even where it is only desired to measure the heart rate. The electronics, signal processing and signal transmission used by these devices are not well adapted to clinical requirements. These defects, however, can be remedied by modification of the electronics in well-known ways. Of greater importance is the fact that the encircling belt is not well adapted to long term wear. In order to secure the device against accidental displacement, the belt must be tightened to a degree that proves objectionable over an extended period. If the belt is loosened one runs the risk of a temporary loss of electrode contact during exercise or while the patient is laying or shifting in bed. Further, the electrodes used in commercial exercise monitors often depend on some degree of perspiration to reduce the electrical resistance of the electrode contact. While perspiration is inevitably present in exercise sufficiently strenuous to merit pulse rate monitoring, its presence cannot be assumed in the clinical setting. Finally, even if tension and electrode issues were resolved, the position of the device across the chest is not optimal for patient and clinician convenience. Application of the device to this region can in some cases constitute an insult to patient dignity. More importantly, the position of the belt may interfere with the application of defibrillator electrodes, the placement of a stethoscope, or other common medical procedures.

It is desirable to expand clinical electronic monitoring to a greater population of patients. This is only practical if an arrangement less unwieldy than traditional clinical ambulatory monitors is adopted. While commercial exercise monitors considerably simplify the monitoring arrangement, they still do not answer well to the needs of such expanded clinical monitoring.

SUMMARY OF THE INVENTION

Accordingly, it is an object of the invention to produce an arrangement of electrodes or other signal sensors or electronics and a mechanical attachment to the patient for said sensors or electronics, which provide convenience, comfort, dignity and low applied cost.

It is a further object of the invention to integrate the electrodes or sensors, electrical connections thereto, mechanical support for the electronics, and where applicable, a power source, into a single, preferably disposable, component.

It is a still further object of the invention to arrange the electrodes or sensors, electrical connections thereto, mechanical support for the electronics, and where applicable, a power source, so that they can be placed securely on the body of a patient with minimal discomfort and insult to dignity.

The invention is a lanyard hung about the neck, from which the medical monitoring electronics is supported in the manner of a pendant. The lanyard comprises integral electrodes or other sensors, auxiliary components and electrical connections thereto.

To the accomplishment of the above and related objects, the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are designated by like reference numerals. The drawings are briefly described as follows.

DETAILED DESCRIPTION OF THE PREFERRED EMBODIMENTS

Figure 1:
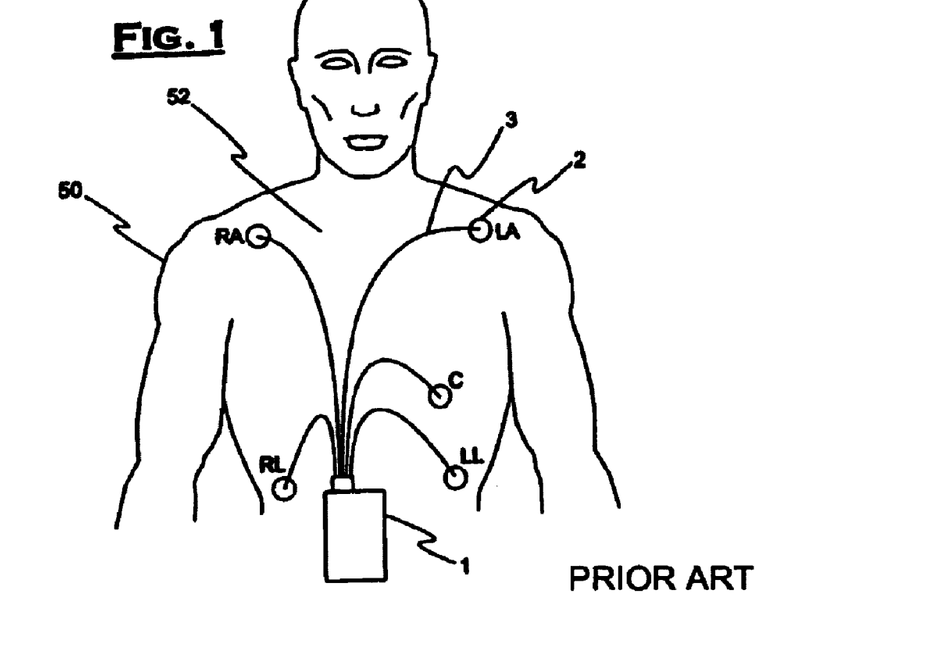
FIG. 1 is a frontal view of a patient connected to a prior art clinical ambulatory monitor.

FIG. 1 illustrates a commonly used prior art clinical ambulatory ECG monitor connected to a chest 52 of a patient 50. Several leadwires 3 extend from a housing 1 to a plurality of electrodes 2 attached to chest 52. Electrodes 2 are labeled RA, LA, RL, C and LL. Housing 1 contains monitoring electronics and is generally supported by a sling (not shown in the figure) or arranged to be clipped to the patient's belt or the waistband of the patient's clothing. This support arrangement is objectionable due to the bulk and weight of the electronics and housing 1 and due to the often encountered difficulty of housing 1 falling loose from its support or attachment.

A rather aggressive adhesive is generally necessary to attach electrodes 2 because they must not only remain securely in contact with chest 52, but must also support the weight and possible tension of leadwires 3. The use of a strong adhesive results in considerable discomfort during removal of electrodes 2 and, in some cases, irritation while they are in place. Further, the numerous leadwires 3 are inconvenient, subject to tangling and may become accidentally detached from electrodes 2. The presence of the wires may also prove disconcerting to patient 50, in that they appear excessively "technical" in nature and may cause patient 50 undue concern over his or her condition.

The electrode arrangements used by the type of prior art monitor illustrated in FIG. 1 are adapted from traditional bedside monitors. A common arrangement is to use five electrodes, as shown in FIG. 1. These are commonly designated RA (right arm), LA (left arm), LL (left leg), RL (right leg), and C (chest), according to the body landmarks near which they are placed. One of the electrodes 2, in this case RL, is designated as a reference electrode. The remaining electrodes 2 are connected to the inputs of several channels of ECG amplifiers. A number of standard ECG vectors, or "leads", can be obtained by taking various combinations of the differential voltages obtained between pairs of electrodes 2. In conventional practice, seven such vectors, commonly designated Lead I, Lead II, Lead III, aVR, aVL, aVF, and C are often used. All seven vectors can be obtained simultaneously, by suitable arrangement of the ECG amplifiers, according to well-known methods.

In a common alternate electrode arrangement, only three electrodes are placed, generally at the locations RA, LA, and LL. In this case, one of the three electrodes is designated the reference electrode, and the ECG amplifier inputs are connected to the remaining two. Although three permutations are possible, giving rise to the ECG vectors Lead I, Lead II, and Lead III, only one vector can ordinarily be obtained at a time in this case.

The use of the reference electrode is necessary in bedside monitor designs, and is somewhat necessary in ambulatory monitors using leadwires, because it greatly facilitates rejection of interference from the AC mains and similar common-mode interference sources. However, if the leadwires are dispensed with, and the monitor electronics and connections are held in intimate proximity to the patient's body, the mechanisms by which common mode interference is injected into the ECG signal are minimized. Under these conditions, operation without a reference electrode becomes more practical.

Figure 2:
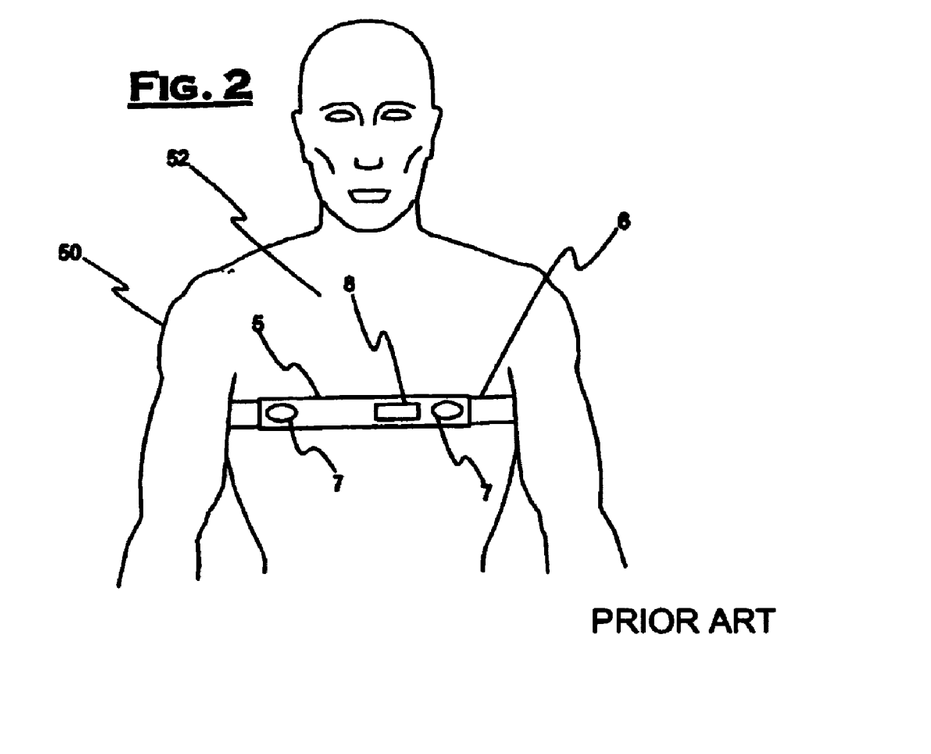
FIG. 2 is a frontal view of a patient wearing a prior art exercise monitor.

The prior art exercise monitor illustrated in FIG. 2 takes advantage of such a two electrode arrangement. Monitor components are contained in a housing 5, which is held in contact with chest 52 of subject 50 by belt 6. The fact of housing 5 touching the skin contains two electrodes 7, which contact the skin and acquire an ECG signal. Electronics 8 are also carried within the housing, and connect to electrodes 7 through wires or other conductive path embedded in the housing (not shown). Because electrodes 7, electronics 8, and their interconnections all lie in very close proximity to the patient's body, there is little opportunity for pickup of common, mode interference, as from the AC mains. This is because the compact arrangement of the electrodes 7, wiring (not shown), and electronics 8 provides very low coupling capacitance to interference sources, while the close proximity to the body provides much larger capacitance to the body. In effect, the patient's body provides a significant measure of electrostatic shielding. As such, given reasonable electrode impedances, such a configuration can operate successfully without an additional reference electrode, and even with a single-ended, rather than the usual differential, ECG amplifier. Therefore, it is possible to operate with just two ECG electrodes. However, as the electrode locations in this device differ from those used in conventional monitoring practice, the waveform morphology of the ECG signal will differ, and some of the diagnostic value of the waveform will be lost. This is not of concern in cases where it is only desirable to measure the heart rate and rhythm, so long as the waveform obtained clearly shows the important features of the ECG signal, such as the R-wave.

While such exercise monitors are far simpler to apply and lack the objectionable leadwires and separate electronics box of clinical ambulatory monitors, they do not answer fully to clinical purposes, even where it is only desired to measure the heart rate. The electronics, signal processing and signal transmission used by these devices are not well adapted to clinical requirements. These defects, however, can be remedied by modification of the electronics in well-known ways. Of greater importance is the fact that encircling belt 6 is not well adapted to long term wear. In order to secure the device against accidental displacement, belt 6 must be tightened to a degree that proves objectionable over an extended period. If belt 6 is loosened, one runs the risk of a temporary loss of electrode contact during exercise or while the patient is laying or shifting in bed. Further, the electrodes used in commercial exercise monitors often depend on some degree of perspiration to reduce the electrical resistance of the electrode contact. While perspiration is inevitably present in exercise sufficiently strenuous to merit pulse rate monitoring, its presence cannot be assumed in the clinical setting. Finally, even if tension and electrode issues were resolved, the position of the device across the chest is not optimal for patient and clinician convenience. Application of the device to this region can in some cases constitute an insult to patient dignity. More importantly, the position of belt 6 may interfere with the application of defibrillator electrodes, the placement of a stethoscope, or other common medical procedures.

Similar to the prior art monitoring device of FIG. 2, the present invention takes advantage of a two electrode system. At the same time, however, the present invention overcomes the above described drawbacks by providing for a pendant monitor that takes advantage of support provided by the shoulder and neck region of the body, which provides a useful monitoring location. The shoulder and neck region is convenient to access without loss of patient dignity. Furthermore, the neck provides a natural means for supporting the weight of a monitor device attached to the electrodes. Electrodes and electronics located in this area are unlikely to be an encumbrance to the patient or disrupt most clinical procedures.

The heart's electrical activity can be modeled as an electric dipole, which varies both in orientation and amplitude over the cardiac cycle. Such a dipole introduces electric field lines connecting its endpoints in the surrounding media. It is these field lines that give rise to the potentials observed at surface electrodes. The potential developed is dependent on the strength of the field, the separation of the electrodes and the angle between the axis of the electrodes and the field lines. The potential is ideally greatest when the field is parallel to the electrode axis and zero when orthogonal. It is for this reason that different electrode orientations produce differing ECG waveform morphologies, since the relative orientations of the electrode axis and the electric field corresponding to a particular feature of the waveform will dictate the amplitude and polarity with which that feature appears on the waveform. Conventional ECG electrode placements have been selected with the intention of providing useful and informative "views" of the heart's electrical activity during the various phases of the cardiac cycle. Note that, according to well-known principles of field mapping, the electric field lines permeate the medium surrounding the dipole causing them. Therefore, although the strongest signals may be obtained with electrodes located near the ends of the dipole, weaker signals are obtained at other locations, including even when the dipole does not lie between the electrodes. There are, of course, cases when no signal is obtained, such as in the case of orthogonality, or when some distortion of the field prevents the field lines from reaching the electrode site.

The body has non-uniform electrical conductivity, and is not infinite in extent. Therefore, the actual body surface potentials are considerably distorted from those that would ideally exist were the heart's electric dipole to induce its electric field lines in a homogenous, infinite medium. Nevertheless, the above generalizations still generally apply. As such, it is possible to obtain ECG signals of diminished amplitude from electrodes located elsewhere than surrounding the heart on the chest. Such locations, however, are preferably on the trunk of the body, as few field lines fringe into narrow extremities. Hence, little signal will be obtained between two electrodes placed on one arm, as few field lines pass into the extremity. On the other hand, a large signal is obtained from one arm to the other, because in this case the arms serve as conductive pathways between opposite sides of the torso, where a strong field exists.

For these reasons, a useful ECG signal can be obtained at the top of the shoulders, near the base of the neck. Morphologically, this signal corresponds roughly to a Lead I conventional ECG waveform, but with some distortion, and reduced amplitude. In a normal individual, it is characterized by a biphasic QRS complex and exaggerated T-wave. However, it is quite satisfactory for basic heart rate and rhythm monitoring. The signal amplitude is greatest when the electrodes are placed on the tops of the opposite shoulders, and gradually decreases as the electrodes are brought toward the base of the neck. The amplitude declines rapidly as the electrodes are moved up the sides of the neck, because only a rapidly attenuated fringe field exists within the neck itself.

Figure 3:
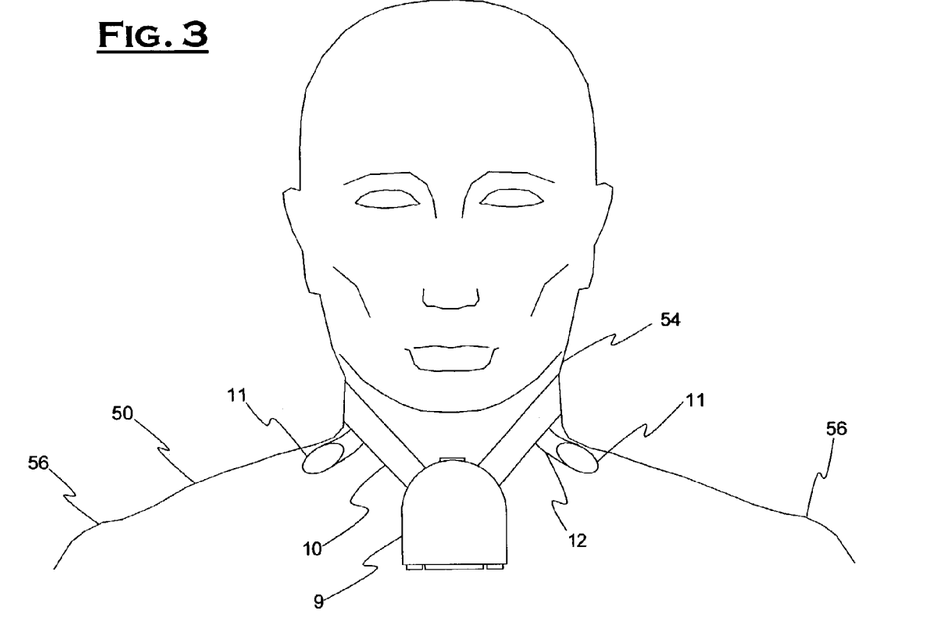
FIG. 3 is a frontal view of a patient wearing the pendant monitor of the present invention around his neck.

The present invention is illustrated in FIG. 3. A monitoring electronics package 9 is attached to, and supported by, lanyard 10. Electronics package 9 hangs from lanyard 10 forming a V shape system with the electronics package 9 at the vertex. V shape is herein defined to include other similar shapes including a U shape. In the preferred embodiment, lanyard 10 is provided with two extensions or flaps 12, each of which carries an electrode 11 or other sensor. Lanyard 10 and flaps 12 are preferably dimensioned such that when hung around neck 54 of patient 50 electrodes 11 are located proximate to the base of patient neck 54, on opposite sides extending somewhat toward shoulders 56.

In an alternate configuration, flaps 12 may be dispensed with, and electrodes 11 placed on an inside surface of lanyard 10, such that they contact opposite sides of the base of neck 54. However, use of flaps 12 provides a more favorable location of the electrodes from the standpoint of signal amplitude, as has been discussed.

In the preferred embodiment, lanyard 10 is detachably connected to electronics package 9. The ability to detach lanyard 10 allows lanyard 10 and its integrated electrodes 11 to be made a disposable, or single-patient use component, while the electronics package 9 can be reused. A lanyard of sufficient length to comfortably encircle a person's neck will not necessarily pass over their head when formed into a closed loop. This problem could be resolved by making lanyard 10 of generous length, such that it will pass freely over the head. However, if lanyard 10 is made too long it will have a tendency to make the electronics package 9 become pendulous, which is undesirable. Therefore, it is preferable to have some means to open lanyard 10 so as to allow it to be wrapped around neck 54. In the preferred embodiment, this is accomplished by making ends 13 and 14 (seen in FIG. 4) of lanyard 10 detachable from electronics package 9.

Figure 4:
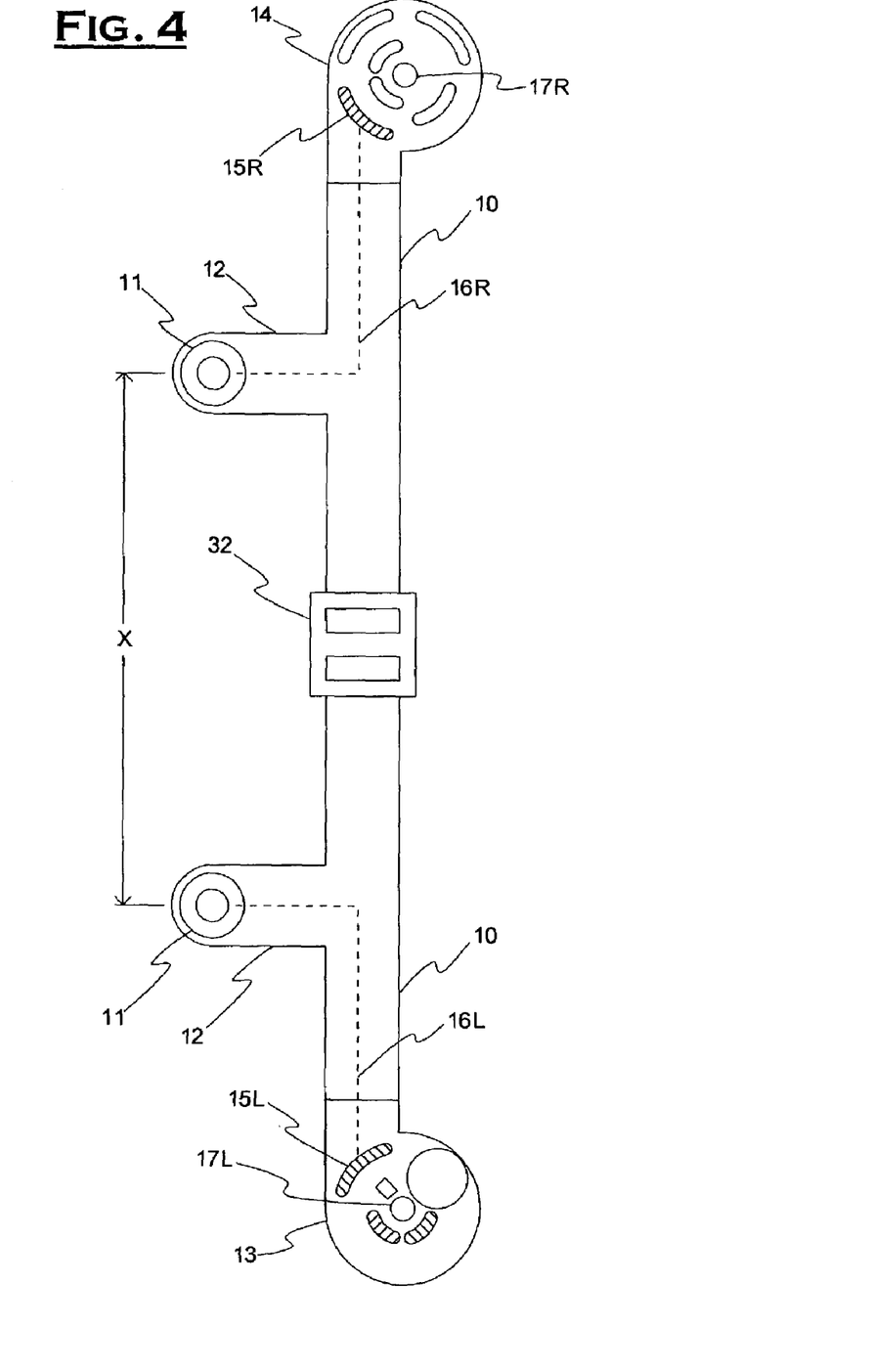
FIG. 4 is a plan view of the pendant monitor lanyard of FIG. 3 is a flattened configuration.

FIG. 4 shows the preferred embodiment of the detachable lanyard assembly. Lanyard 10 includes two flaps 12, each bearing ECG electrodes 11, separated by a suitable distance X such that electrodes 11 rest approximately on top of a person's shoulders, proximate to the base of the neck, when lanyard 10 is closed or looped around the patient's neck.

The human neck varies significantly in size. In order for electrodes 11 to be positioned exactly consistently despite variations in neck size, variation of the electrode separation X is preferred. A length adjustment device 32 may be placed in the region between electrodes 11 to permit adjustment of distance X. Length adjustment device 32 may comprise an adjustable buckle. Alternatively, one portion of lanyard 10 may be provided with several perforations disposed along its length, any one of which can be mated with a corresponding stud on the other portion, effecting adjustment in length. The relative position of the portions can also be set by use of hook and loop fasteners, pressure sensitive adhesive, buttons, snap fasteners, or other similar means. The ability to adjust the length of lanyard 10 also proves useful when it is desired to deliberately alter the positions of the electrodes, as in cases where interference with a bandage, cast, or other medical device already placed on the patient must be avoided.

In an alternate embodiment, no buckle or other adjustment device is provided. Varying size requirements may be accommodated by manufacturing the lanyard 10 in various sizes, differing in dimension X. A small number of sizes is required to cover the entire range of neck sizes. A particular lanyard with a given dimension X will result in optimal electrode positioning for a certain neck size. If this same lanyard is placed on a subject with a considerably smaller neck, the electrodes will become displaced somewhat forward, moving down from the top of the shoulders toward the frontal surface of the chest. If this lanyard is placed on a person with a larger neck, the electrodes will be displaced from the top of the shoulders toward the person's back. However, neither of these displaced positions of the electrodes materially affects the quality or utility of the ECG signal obtained, provided the displacement is not very great. Therefore, a single size of lanyard can accommodate a considerable range of neck sizes, subject to acceptable displacement of electrodes 11.

In addition to providing superior support of the electronics, lanyard 10 of the present invention is generally of shorter circumference or length than belt 6, in an unfastened state, found in the prior art of FIG. 2. This is a consequence of the fact that the circumference of an individuals neck is considerably smaller than that of their torso. In cases where lanyard 10 is a disposable component, this results in a savings of not only the material used in construction, but also permits smaller and more convenient packaging and storage of the disposable component. The inclusion of electrodes 11 and associated conductors 16 within lanyard 10 additionally provides an advantage over the prior art of FIG. 2, where these components are part of electronics housing 5. Because electrodes 11 contact the patient, it is desirable that these components be disposable from the standpoint of sanitary practice. This is facilitated by their removal from the electronics housing and integration with lanyard 10.

Electrodes 11 may be of ordinary types, such as sponge or hydrogel types. However, unlike the prior art, they do not require a highly aggressive adhesive, as they are not required to support the weight of a heavy leadwire. The skin-contact surface of lanyard 10 itself and flaps 12 may be wholly or selectively coated with a mild adhesive, or may be coated with or comprised of material promoting friction or adhesion against the skin, to help prevent lanyard 10 from shifting in position and, thereby, mechanically straining electrodes 11.

Ideally, lanyard 10 should lie flat and conform to the body surface, without being twisted or buckled. An attempt to bend a flat, ribbon-like lanyard transversely will tend to cause it to buckle or twist. Therefore, rather than attempting to bend lanyard 10 to meet electronics package 9, electronics package 9 accepts ends 13 and 14 of lanyard 10 at their natural angle of approach. This is accomplished by providing for an articulating attachment of lanyard ends 13 and 14 to electronics package 9.

In FIG. 4, lanyard ends 13 and 14 are provided with central holes 17R and 17L, which engage an anchor post 28 (FIG. 5B) in electronics package 9. Ends 13 and 14 of lanyard 10 are free to pivot about anchor post 28, allowing accommodation for the natural angle of lanyard ends 13 and 14 when placed on patient 50. Adjustment of the attachment angle is only necessary at the time the device is placed on a person; at such time the angle should be set such that lanyard 10 lies flat and smooth. Once the angle is set, some degree of friction restricting further movement of the articulated connections is desirable, as this improves the mechanical stability of the device. It is preferred that the angle between lanyard ends 13 and 14, represented by arrow A, be adjustable by at least 15 degrees. Rotation of either or both ends 13 and 14 has the effect of changing angle A.

Lanyard 10 and flaps 12 may be composed of any material and have any accommodating geometry, however, a flexible ribbon-like material, such as fabric, textile braid, paper, soft plastic; or similar materials, or combinations of these materials, is preferred. Lanyard ends 13 and 14 may be stiffened, such as by lamination with stiff plastic sheet or heavy paper, to permit secure attachment to electronics package 9.

In the preferred embodiment, attaching lanyard ends 13 and 14 to electronics package 9 provides for both a mechanical and electrical connection. Mechanically, central holes 17L and 17R engage anchor post 28 (FIG. 5B) and ends 13 and 14 are enclosed in electronics package 9 in a clamshell manner (see FIG. 6B). Electrically, connection of electrodes 11 is provided by means of annular conductive contact regions 15L and 15R, which are connected to electrodes 11 by means of conductive paths 16L and 16R, shown as ghost lines, integrated into or otherwise attached to lanyard 10. At least a portion of one or both conductive paths 16 may be composed of a material having a high resistivity, such as carbon ink, so as to provide sufficient resistance in series with electrodes 11 as to facilitate protection of electronics package 9 from transient voltages induced in the electrode circuit during patient defibrillation.

Conductive paths 16R and 16L between electrodes 11 and electrical contact regions 15R and 15L are preferably integrated into lanyard 10, such as by lamination between layers comprising lanyard 10. Conductive paths 16L and 16R may take the form of a fine wire, a metal foil strip, a conductive polymer, conductive ink deposited by silkscreen or other printing process, or a flexible printed circuit board. Lanyard ends 13 and 14 may be composed of, or stiffened by, thin printed circuit boards, in which case the foil pattern of the circuit board may constitute contact regions 15L and 15R.

Electrical contact points 29 (FIG. 5B) connected to a circuit assembly 30 in electronics package 9 contact the conductive contact regions 15L and 15R, and thus, provide a pathway between electrodes 11, which acquire the patient signal, to circuit assembly 30, which processes, stores or transmits the signal, or provides any combination of these functions.

According to the intended program of patient monitoring, electronics package 9 may be designed to accomplish any of a number functions. For example, it can operate in the manner of a holter monitor, where it only stores patient signals. It could operate in the mode of a conventional telemetry transmitter, where the full waveform of the patient's signal is transmitted to a remote location. It could alternately operate in the mode of an exercise monitor, in which the heartbeat is detected, and a signal marking each heartbeat is transmitted to a remote device. Further, it could operate by locally processing and analyzing the patient signal, and transmitting only summary data or analysis results to a remote device. Note that not only the ECG, but any signal related to cardiac activity, such as the photoplethysmograph signal, heart sounds, mechanical pulse signal, and others can be used as the basis for detecting the heartbeat. Further, by the introduction of other sensor types in addition to, or instead of, electrodes 11, other types of physiologic signals may be stored or manipulated by electronics package 9, as described for the ECG signal.

End 13 or 14 of lanyard 10 may include a battery 18, or alternate power source, to run the device. In the preferred embodiment, the battery is a lithium coin cell, such as the standard type CR2032, produced by numerous manufactures. However, the use of other types of batteries is contemplated, including multiple cells in series or parallel, other chemistries such as zinc-air, and other planar battery structures, such as the flat Polapulse batteries manufactured by Polaroid Corporation (Waltham, Mass.).

Alternately, battery 18 may be incorporated into electronics package 9. However, in the preferred embodiment, the battery is attached to the disposable lanyard 10, so that a fresh battery is automatically provided when a new lanyard 10 is placed on a patient and connected to electronics package 9. Since lanyard 10 may be designed for single patient use, a number or other identifier assigned to the lanyard 10 at the time of manufacture becomes a convenient patient identifier. In the preferred embodiment, this identifier is stored in electronic form, and can be automatically read from lanyard 10 by electronics package 9.

Figure 5A:
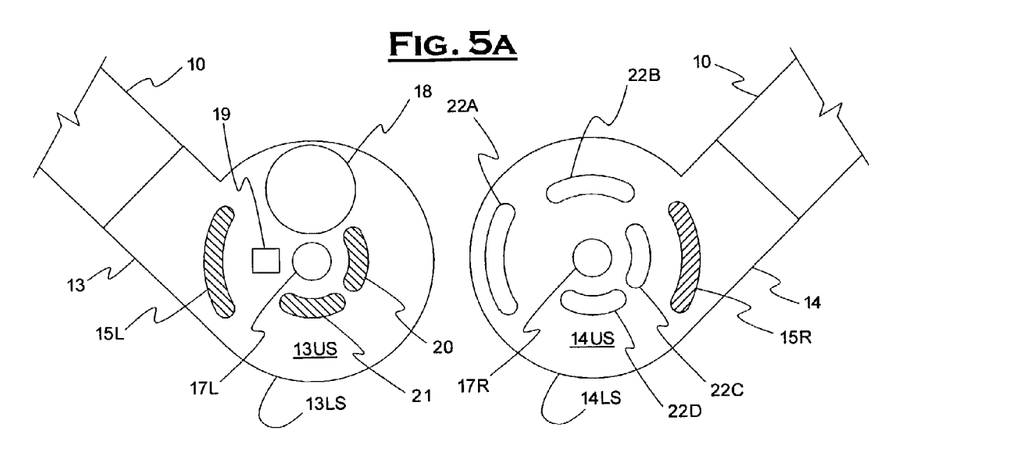
FIG. 5A is a plan view of the articulated ends of the lanyard portion of the pendant monitor, which fit into the electronics housing.

FIG. 5A illustrates the details of the preferred embodiment of lanyard ends 13 and 14. End 13 comprises a battery 18, an electronic identifier 19, an upper surface 13US, a lower surface 13LS, a central hole 17L and annular electrical contacts 15L, 20 and 21. End 14 comprises an annular electrode contact 15R, an upper surface 14US, a lower surface 14LS, a central hole 17R and annular slots 22A, 22B, 22C and 22D. Lanyard ends 13 and 14 are shown positioned as they would be after looping lanyard 10 around the neck of a person but before being connected to electronics package 9, i.e. surfaces 13US and 14US both face up.

Identification device 19 is preferably an electronic memory device, such as the DS2401 Silicon Serial Number, manufactured by Dallas Semiconductor (Dallas, Tex.). This device contains a unique identification number which can be read electronically by a single wire serial data interface, established preferably through contact 21. The common or ground connection used by this device may be made by means of the battery contact or electrode contact 15. Other types of memory devices may be used. Although the DS2401 requires no explicit power source, battery 18 may supply standby power to other types of identification devices. For example, a device utilizing status RAM for data storage could be kept energized, even when not connected to electronics package 9, by means of battery 18.

Annular contact segments 15L, 15R, 20 and 21 may take the form of a metal foil, conductive polymer, or conductive ink, deposited by silkscreen or other printing process, or any other appropriate conductive contact known in the art.

Figure 5B:
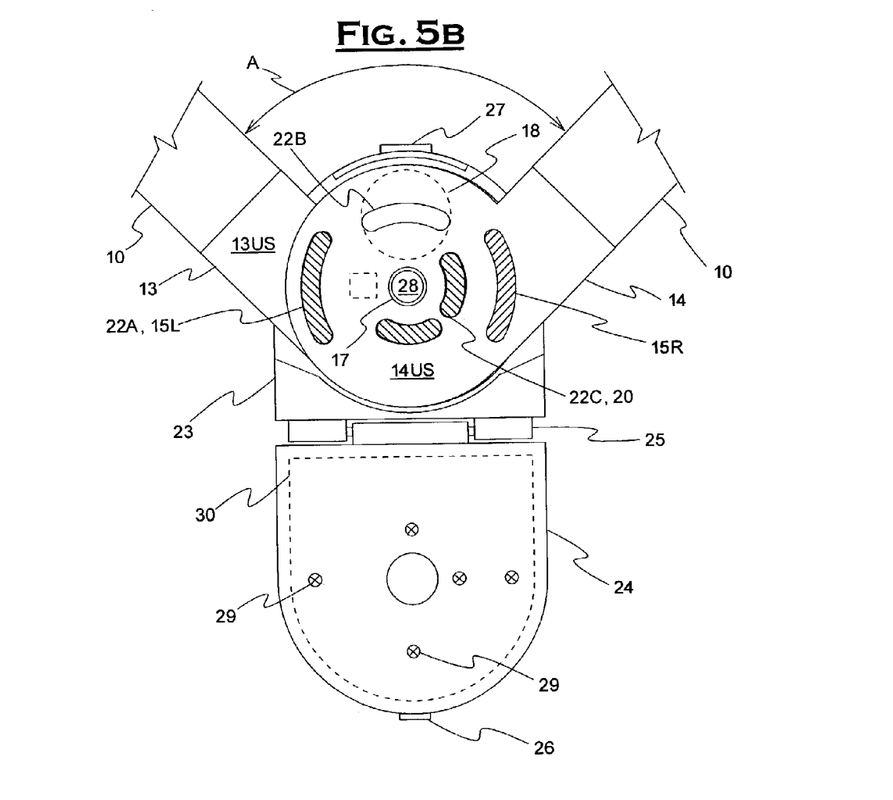
FIG. 5B is a plan view of the ends of the lanyard of FIG. 5A in position in the open electronics housing.

Lanyard ends 13 and 14 could be placed in the electronics package 9 side by side, much as they are illustrated in FIG. 5A, on independent anchor posts. However, the preferred embodiment makes use of a common anchor post 28, as is shown in FIG. 5B. This figure shows ends 13 and 14 of lanyard 10 placed into opened electronics package 9 for the purpose of attaching it to lanyard 10. Electronics package 9 consists of a cover 23 and body 24, connected by hinge 25, and is capable of being closed and secured by latch tongue 26 and latch receiver 27, in the manner of a clamshell.

End 14 is placed over end 13, i.e. end 13 is sandwiched between end 14 and cover 23. Cover 23 is provided with anchor post 28, which engages the central holes 17L and 17R of ends 13 and 14. End piece 13, containing contacts 15, 20, and 21, is first placed over anchor post 28 in housing cover 23. Next, end piece 14 is placed over end piece 13 by disposing anchor post 28 within central hole 17R. End piece 14 is provided with suitable apertures 22A–22D which permit access to the contact regions 15, 20, and 21, as well as the terminal area of battery 18. The opposing half of the electronics package housing, base 24, is provided with several electrical contact points 29, connected to circuit assembly 30, which contact the various electrical contact regions of end pieces 13 and 14 when electronics package 9 is closed, i.e. when latch tongue 26 snaps over or mates with latch receiver 27. Battery 18 is shown in ghost lines as it is underneath end piece 14, although accessible to electrical contact through aperture 22B. Contact regions 15L, 15R, 20 and 21, and apertures 22A–22D, have annular shapes but may take on other shapes so long as they are suitably dimensioned to permit articulation as discussed above, such that some portion of each annular contact region is accessible to its corresponding contact point 29 over a predetermined range of angular rotation of ends 13 and 14 about anchor post 28.

Figure 6A:
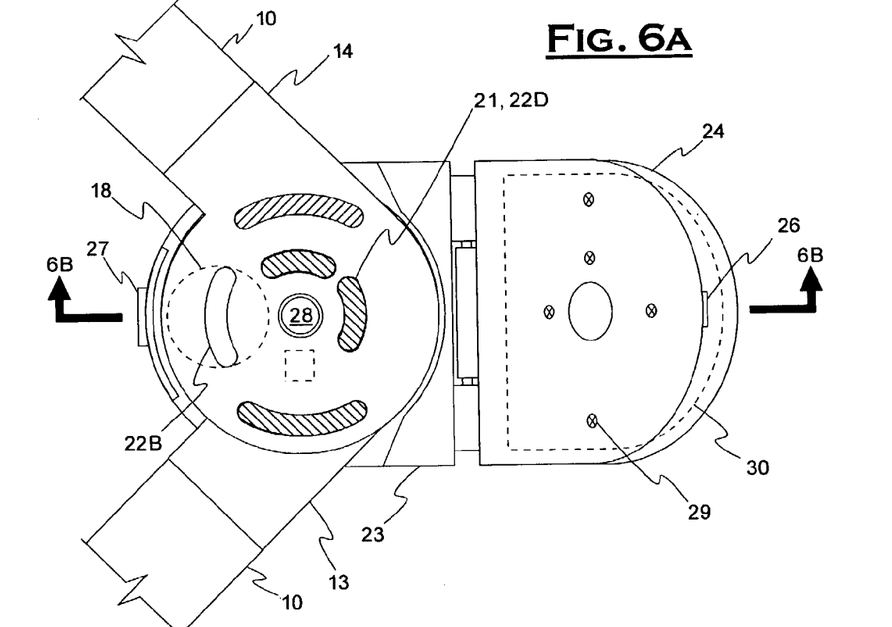
FIG. 6A is a plan view of the ends of the lanyard and the partially closed electronics housing.
Figure 6B:
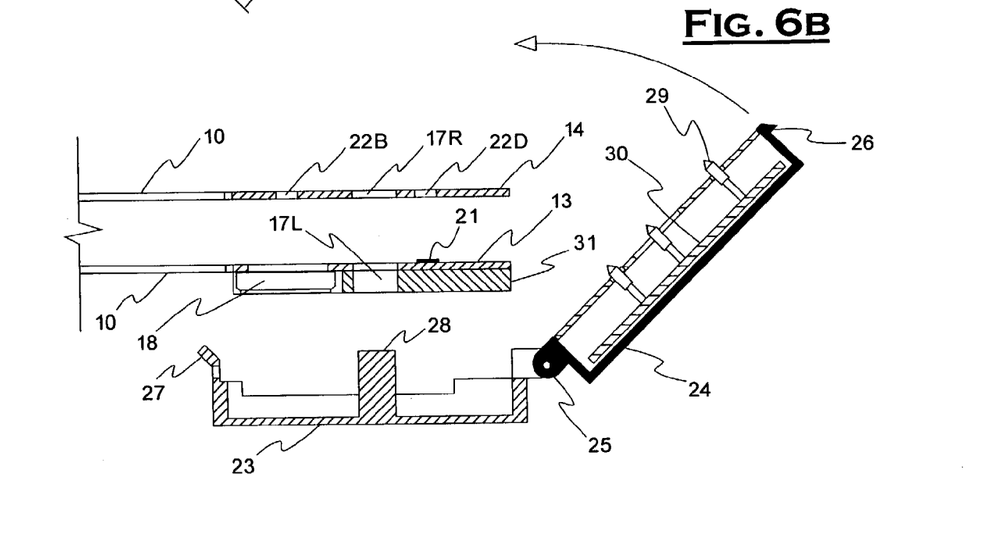
FIG. 6B is a longitudinal cross sectional view of the ends of the lanyard and housing taken along lines 6B—6B.

FIG. 6A shows another view of the end pieces in electronics package 9, shown in a partially closed position. A sectional view along lines 6B—6B, clarifying the arrangement of the components, is illustrated in FIG. 6B. For clarity, ends 13 and 14 have been shown lifted out of housing cover 23 in the sectional view. To complete attachment of electronics package 9 to lanyard 10, end pieces 13 and 14 would be dropped fully down over anchor post 28, and housing body 24 pivoted on hinge 25 in the direction indicated by the curved arrow, until electronics package 9 is closed, and latch tongue 26 becomes retained in latch receiver 27. This operation brings contact points 29 to bear on their associated annular contact regions on ends 13 and 14. The sectional view cuts through annular contact 21 and battery 18, located on end 13. Note that apertures 22B and 22D are provided on end piece 14 directly above these components, to permit access by the associated contact points 29. To provide a flat surface on end piece 13, despite the thickness of battery 18 and identification device 19, spacer disk 31 may be attached to end piece 13. Spacer disk 31 may be cut out to accept the thickness of battery 18, identification device 19, and any other auxiliary components which may be attached to end piece 13.

Several variations of the construction depicted in the figures are possible. Anchor post 28 may advantageously be made considerably longer than is necessary to engage both central holes 17R and 17L, as the additional length helps the user to position the end pieces over anchor post 28 and maintain them in position while closing electronics package 9. A suitable recess may be required in housing body 24 to receive the excess length of anchor post 28. The construction can also be inverted, in which anchor post 28 projects from housing body 24. In this case, ends 13 and 14 are first dropped over anchor post 28 protruding from body 24, and then cover 23 is closed over them. Alternatively, it is possible to dispense with central holes 17R and 17L and anchor post 28 altogether, and rely on the circular portion of the outer periphery of ends 13 and 14, together with the internal shape of cover 23, to locate ends 13 and 14, while still allowing articulation.

To aid in keeping end pieces 13 and 14 correctly positioned within housing cover 23, various retention features may be added. For example, anchor post 28 may be furnished with an undercut, barbs, or similar feature, which catches central holes 17R and 17L of ends 13 or 14. Alternatively, central holes 17R and 17L and anchor post 28 may be dimension to provide a snug fit. Also, ribs or projections may be added to an internal periphery of housing cover 23 to assist in retaining ends 13 and 14 by engaging their outer periphery.

Figure 7:
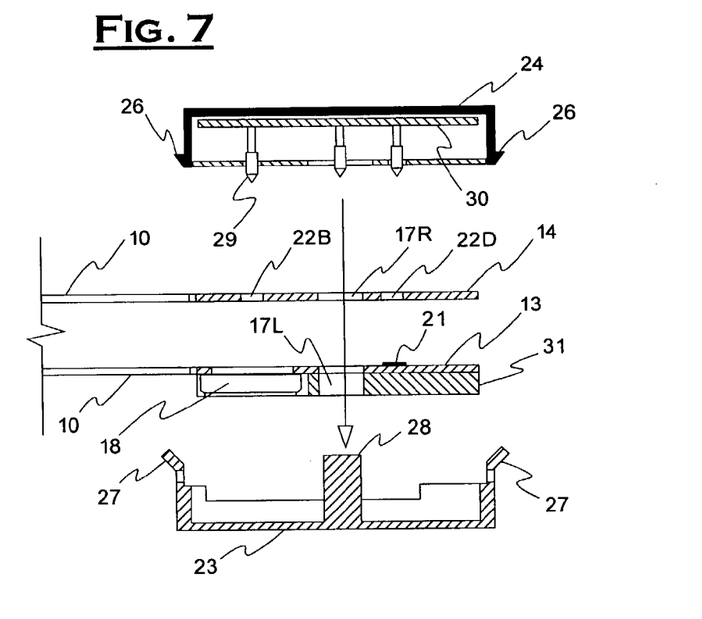
FIG. 7 is a longitudinal cross sectional view of an alternate embodiment of the electronics housing of FIG. 6, not employing a hinge.

Hinge 25 may take various forms, including a living hinge integral with the plastic comprising electronics package 9. Electronics package 9 may be constructed without a hinge, as illustrated in FIG. 7. In this case, body 24 and cover 27 are not hinged together, but are separate components. Ends 13 and 14 are first dropped over anchor post 28 of housing cover 23 and then housing base 24 is engaged by perpendicular motion, as indicated by the arrow in the figure, and becomes secured by latch tongues 26 and latch receivers 27. To avoid accidental loss of cover 23, it can be integrated with the disposable lanyard assembly. For example, it can be made a captive part of end piece 13, while still allowing the angular rotation necessary for articulation. For either construction, latch tongue 26 and latch receiver 27 may be replaced by any of several well-known closure devices. These include threaded fasteners, cam or "quarter-turn" fasteners, magnetic catches, friction locks, pressure sensitive adhesives, hook and loop fasteners, or any similar devices. More than one latching point may be provided. The location of the latching point may differ from that shown, such as by being located in the center, rather than periphery, of the housing.

The identifier stored in identification device 19 may also be printed on a label affixed to lanyard 10. This label may be human readable, machine readable, as in the case of a bar code, or both. Such a label may be placed anywhere on the device. However, in the preferred embodiment it is placed on the underside of spacer disk 31, as seen in FIGS. 6A, 6B or 7. Cover 23 may be composed of a transparent material, or furnished with a window, such that the label can be read through the cover while the monitoring device is worn by a person. In this case, electronics package 9 also serves the purpose of an identification badge or pendant. In the arrangement shown in FIG. 7, cover 23 may be integrated with end piece 13, as has been discussed. In this case, cover 23 need not be transparent or windowed, as the identification label can be placed on an outer surface of captive cover 23.

The need for apertures 22A–22D may be eliminated if contact points 29 are provided on cover 23 as well as body 24 of the electronics package housing. The annular contact regions 15L, 20 and 21 of end 13 would then be placed on surface 13LS, as opposed to surface 13US, such that they touch the contact points provided in cover 23. In this case the spacer disk 31 may advantageously be placed between ends 13 and 14.

In an alternate embodiment of articulated ends 13 and 14, annular contact regions 15L, 15R, 20 and 21 are eliminated, and anchor post 28 becomes the contact and mates with a receptacle in electronic package 9. Various forms of this arrangement, differing in the number of contact circuits provided, are shown in FIGS. 8A–8C.

Figure 8A:
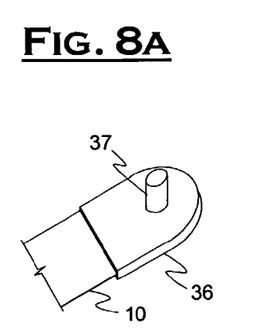
FIG. 8A is a perspective view of an alternate embodiment of the articulated lanyard ends including a conductive anchor post.

FIG. 8A illustrates lanyard 10 attached to modified end 36, equipped with an electrically conductive contact stud 37. Stud 37 serves both the function of an anchor post, allowing articulation, and an electrical contact. Although the figure shows the male portion of the connection on end 36, and presumes the corresponding female portion to be on electronics package 9, it is understood that the configuration may be inverted, with the male portion on electronics package 9 and the female portion on end 36. The male and female portions may take on various particular shapes. For example, stud 37 may assume the form of the male portion of a snap fastener and the receptacle the mating female portion of a snap fastener. The arrangement shown in FIG. 8A is suitable when only a single circuit is to be connected, for example, from an electrode. When multiple connections are required, the simple stud may be replaced by a coaxial contact arrangement.

Figure 8B:
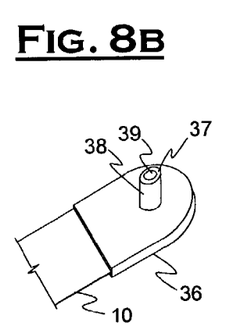
FIG. 8B is a perspective view of an alternate embodiment of the articulated lanyard ends including a coaxial conductive anchor post.

FIG. 8B illustrates a lanyard end 36 with a stud 37, now having a coaxial contact. Stud 37 comprises an outer contact portion 38 and an inner contact portion 39, permitting two circuits to be connected.

Figure 8C:
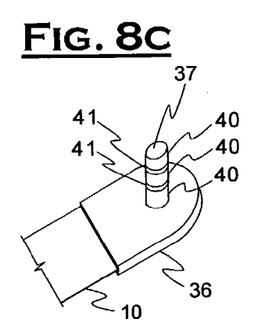
FIG. 8C is a perspective view of an alternate embodiment of the articulated lanyard ends including a conductive anchor post having three electrical contacts.

FIG. 8C illustrates a lanyard end 36 having a stud 37 divided into several contact rings 40, separated by insulating regions 41, in the manner of an ordinary headphone plug. Although the figure shows three circuits, it is understood that more or fewer circuits could be provided.

Planar ends 13 and 14 with the several annular contact regions of the preferred embodiment facilitate provision of large numbers of contacts, such as when auxiliary components must be provided with contacts, in addition to electrodes. However, the alternate embodiments of FIGS. 8A–8C, while more restricted in the number of contacts, are better adapted to waterproof or water resistant construction. Hybrid constructions, employing both a central contact stud of any of the forms discussed, plus one or more annular contact regions on the face of end 36, are anticipated as well.

Whenever any lanyard is placed about a person's neck, the risk of accidental strangulation or other injury must always be considered. Should the lanyard become entangled or otherwise engaged with some other object, machinery, or the like, injury may result. In order to prevent such injury, lanyard 10 may be designed with a breakaway feature, such that this feature becomes disengaged before a dangerous degree of tension can be produced in lanyard 10.

There are many commonly known methods of providing a breakaway feature. The tensile strength of the lanyard material can be selected so as to avoid danger. If lanyard 10 is composed of a stronger material, it can be equipped with a weakening notch or perforations, designed such that the area so weakened will fail at the desired tension. Length adjustment device 32 can be designed to release or fail at a predetermined tension. The strength of attachment of lanyard 10 to ends 13 and 14, or the strength of ends 13 and 14, can be suitably chosen. Furthermore, the engagement of lanyard ends 13 and 14 into electronics package 9 can be designed to release or fail at a predetermined tension.

The use of a flat, ribbon-like lanyard 10 provides good mechanical stability of the invention when placed on a person. Further, it affords the possibility of coating the skin-contact side of lanyard 10 with adhesive or friction-promoting material, further enhancing stability. However, a lanyard of substantial width does not flex readily transversely. Accordingly, if such a lanyard is to lie flat and smooth, the attachment of the lanyard to the electronics unit 9 should be articulated, as discussed. The articulated attachment adds some degree of complexity, particularly if waterproof or water resistant construction is required.

In contrast to a ribbon, a thin cord, particularly one of circular cross section, flexes with equal ease in all directions. If lanyard 10 were constructed of such a cord, articulated connections to electronics package 9 would no longer be required, as the cord could easily flex to meet attachments of some fixed angle.

Figure 9:
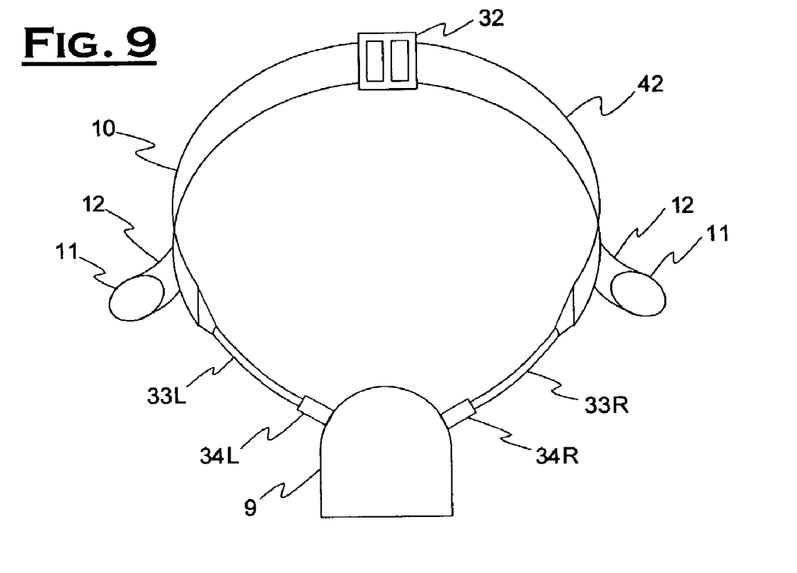
FIG. 9 is a perspective view of an alternate embodiment of the lanyard assembly, employing flexible cords.

It is possible to construct the entire lanyard assembly of such a cord. However, some measure of the mechanical stability afforded by the flat ribbon can be preserved by a composite construction. An alternate embodiment of the invention incorporating such a composite construction is illustrated in FIG. 9. Lanyard 10 consists of a flat ribbon portion 42 and two flexible cords 33L and 33R. As in the other embodiments, lanyard 10 is furnished with electrodes 11, or other sensors, and may additionally have flaps 12. Lanyard 10 may also be furnished with length adjuster 32. Cords 33L and 33R may be provided in various ways. A cord or tubing may be attached to the flat ribbon portion 42 of the lanyard 10. Alternately, flat ribbon portion 42 itself may be folded, rolled, or twisted into a tube on the ends.

Cords 33L and 33R each contain a suitable electrical conductor for electrodes 11, as well as any other electrical devices attached to the lanyard assembly. Cords 33L and 33R are equipped with connectors 34L and 34R on one end, which mate with sockets on electronics package 9, providing electrical and mechanical attachment. Connectors 34L and 34R may use any of the common forms of electrical contacts, such as pin and socket, butt, bellows, and others familiar to those skilled in the art. Any of several common retention means, including friction, detent, threads, bayonet, and similar means may be used to secure connectors 34 into electronics package 9. Auxiliary devices, such as battery 18 or identification device 19, may be imbedded in connectors 34, or located elsewhere on the lanyard assembly, and provided with suitable conductors to, and contacts in, the connectors. The use of two connectors 34L and 34R permits lanyard 10 to be opened for ease of placement about the neck, and therefore allows for use of a lanyard too short to pass over the head when closed.

Figure 10:
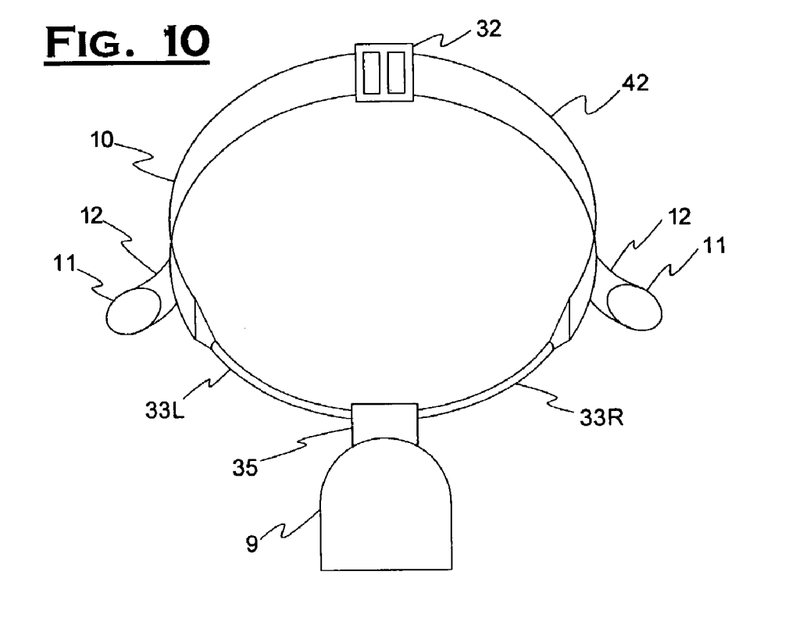
FIG. 10 is a perspective view of an alternate embodiment of the lanyard assembly with a single attachment connector.

In FIG. 10, a single common connector 35 to electronics package 9 is used, with both cords 33L and 33R attached to this single connector. In this case, lanyard 10 may be made long enough to always be capable of passing over the head, or alternate means of opening the lanyard may be provided. Length adjuster 32 may provide the means of opening the lanyard, or a similar device not providing length adjustment, but merely allowing lanyard 10 to be separated, may be employed. Alternately, one of cords 33L and 33R may be made detachable from common connector 35.

Although the preceding examples have shown only two electrodes 11 as the physiological signal sensors, other configurations are anticipated, and additional sensors may be added. While ECG signal acquisition without a reference electrode is possible, certain applications of the invention may benefit from the improved signal possible with such an electrode. A third electrode may therefore be placed at any convenient skin-contact location on lanyard 10, and be furnished with suitable conductors to, and contacts in, the end pieces. Similarly, the lanyard assembly may be furnished with additional active electrodes 11 and longer flaps 12, such that these electrodes may be placed on various portions of the chest, such as to approximate conventional three or five electrode monitoring configurations.

Other types of sensors, besides ECG, are contemplated as part of the invention. A portion of the lanyard 10 contacting the skin may be furnished with a thermistor or other temperature sensor, allowing the body temperature to be monitored. A portion of lanyard 10 contacting the skin may be equipped with a reflectance mode pulse oximetry sensor, allowing the patient's blood oxygen saturation to be monitored. Alternately, an extension, similar to flaps 12, may be added to integrate a transmission mode pulse oximeter sensor placed on the earlobe. A similar extension may be used to integrate various sensors placed within the ear canal, such as a tympanic temperature sensor or ear canal pulse oximeter. In all cases, additional sensors are provided with suitable conductors in lanyard 10, and contacts in the end pieces, allowing their signals to be communicated to electronics package 9.

Electronics package 9 may also be furnished with various sensors, in addition to the customary signal processing and related electronics. For example, an accelerometer and inclinometer may be provided to detect activity and posture of the patient, providing useful information for correlation with the other vital signs.

While the preferred embodiments comprise a disposable, or single-patient use, lanyard assembly and reusable electronics package 9, the ever-lowering cost of electronics makes a fully disposable device feasible in certain applications of the invention. In this case, electronics package 9 need not be detachable from the lanyard 10, and the complexity of connectors 34L and 34R may be eliminated. If the lanyard is made sufficiently long to pass over the head when formed in a closed loop, all means of detachment of any portion of lanyard 10 may be eliminated. If a shorter lanyard, which must be opened to pass over the head in at least some cases, is to be used, at least one point of detachment must be provided. This may be combined with length adjustment device 32, and need not involve the interruption of any electrical conductors.

Lanyard 10 and electronics package 9 are preferably arranged such that the electronics become active, such as by connection of battery 18, automatically only when the detachable portions of the lanyard are engaged. In this way, no drain of the battery can occur before the device is placed on a person, and the device is automatically set in action once placed on a person. This occurs naturally with the construction illustrated in FIG. 5, since battery 18 makes connection with the electronics package 9 when the electronics package housing is closed about ends 13 and 14 of the lanyard 10. However, this feature may be provided in other constructions by arranging any attachment point to close an electrical circuit when engaged, such as by closing a switch, or by engagement of electrical contacts and conductors carried through the attachment point.

Thus, it is understood, that while particular examples have been described, it should be apparent to those skilled in the art that many modifications can be made without departing from the scope and intent of the invention. Accordingly, the invention is not limited to the specific embodiments thereof, except as defined in the appended claims.

What is claimed is:

1. A monitoring device, comprising:
   a lanyard;
   a power source disposed on the lanyard;
   one or more physiological sensors attached to the lanyard; and
   an electronics package removably connectable to the lanyard, whereby power is supplied from the power source to the electronics package upon connection of the electronics package to the lanyard.

2. The monitoring device as claimed in claim 1, wherein the lanyard has a pair of free ends, and the power source includes a battery positioned in one of the free ends.

3. A monitoring device, comprising:
   a lanyard having a pair of free ends;
   one or more physiological sensors connected to the lanyard; and
   an electronics package connectable to the free ends of the lanyard in an articulating fashion with one free end of the lanyard directly connected to the electronics package and the other free end of the lanyard directly connected to the electronics package so that, when the electronics package is hung from the lanyard, the electronics package and the lanyard form a V shape having a vertex, with the electronics package at the vertex of the V-shape.

4. A monitoring device, comprising:
   a lanyard;
   one or more physiological sensors connected to the lanyard;
   an electronics package removably connectable to the lanyard; and
   at least one conductive pathway integrated with the lanyard so that upon connection of the electronics package to the lanyard, an electrical connection is made between the sensors and the electronics package.

5. The monitoring device as claimed in claims 1 or 3 or 4, wherein the sensors comprise two or more electrocardiogram electrodes.

6. The monitoring device as claimed in claims 1 or 3 or 4, wherein the sensors include a temperature sensor.

7. The monitoring device as claimed in claims 1 or 3 or 4, wherein the sensors include a pulse oximetry sensor.

8. The monitoring device as claimed in claims 1 or 3 or 4, wherein the lanyard at least partially comprises a flat ribbon.

9. The monitoring device as claimed in claims 1 or 3 or 4, wherein the lanyard at least partially comprises a cord.

10. The monitoring device as claimed in claim 4, wherein the conductive pathway includes conductors embedded between layers of flat ribbon.

11. The monitoring device as claimed in claims 1 or 3 or 4, wherein the lanyard comprises a substantially elongated material having a longitudinal axis and one or more flaps projecting at an angle from the longitudinal axis, the sensors being directly connected to the flaps.

12. The monitoring device as claimed in claims 1 or 3 or 4, wherein the lanyard includes length adjustment means for adjusting the length of the lanyard.

13. The monitoring device as claimed in claims 1 or 3 or 4, wherein the lanyard includes means for enhancing the contact adhesion of the lanyard to a patient.

14. The monitoring device as claimed in claims 1 or 4, wherein the lanyard includes a pair of free ends and a connector, the free ends being connected to the electronics package, and the connector being connected between the free ends of the lanyard and allowing for separation of the lanyard into two or more segments.

15. The monitoring device as claimed in claims 1 or 3 or 4, wherein the lanyard separates into two or more segments upon application of a predetermined threshold tension to the lanyard.

16. The monitoring device as claimed in claims 3 or 4, further comprising a power source connected to the lanyard for supplying power to the electronics package.

17. The monitoring device as claimed in claims 1 or 3 or 4, further comprising identifier means connected to the lanyard.

18. The monitoring device as claimed in claims 1 or 4, wherein the electronics package is connected to the lanyard in an articulating fashion.

19. The monitoring device as claimed in claims 1 or 3 or 4, wherein the electronics package comprises a transmitter.

20. The monitoring device as claimed in claims 1 or 3 or 4, wherein the electronics package comprises a processor.

21. The monitoring device as claimed in claims 1 or 3 or 4, wherein the electronics package comprises a memory unit.

22. The monitoring device as claimed in claims 1 or 3 or 4, wherein the lanyard comprises an electronic identification tag.

23. The monitoring device as claimed in claims 1 or 4, wherein the lanyard includes a pair of free ends and the electronics package includes connection means for securing the free ends of the lanyard to the electronics package, the connection means allowing for articulation of the free ends of the lanyard relative to the electronics package.

24. The monitoring device as claimed in claims 1 or 3 or 4, wherein the lanyard includes a pair of free ends and the electronics package includes connection means for securing the free ends of the lanyard to the electronics package, the connection means allowing for articulation of the free ends of the lanyard relative to the electronics package, the free ends of the lanyard including electrical contacts for maintaining an electrical connection between components of the electronics package and the sensors for at least 15 degrees of articulation.

25. The monitoring device as claimed in claims 1 or 3 or 4, wherein the lanyard includes a pair of free ends each having a hole, and the electronics package includes a housing having a post, the post being disposed within the hole in each free end of the lanyard.

26. The monitoring device as claimed in claims 1 or 3 or 4, wherein the lanyard includes a pair of free ends each having a hole, and the electronics package includes a housing having a post, the post being disposed within the hole in each free end of the lanyard, and at least a portion of each free end of the lanyard and at least a portion of the housing having a circular shape.

27. The monitoring device as claimed in claims 1 or 3 or 4, further comprising means for determining the activity level of a patient.

28. The monitoring device as claimed in claims 1 or 3 or 4, further comprising means for determining the orientation of a patient.

29. A method for monitoring a subject, comprising:
(a) providing a monitoring device having a lanyard, one or more physiological sensors attached to the lanyard and an electronics package having a first housing connected to the lanyard and a second housing removably connectable to the first housing, the first housing including an electronic circuit and the second housing including a power source removable from the second housing;
(b) suspending the monitoring device from the subject's neck;
(c) connecting the second housing to the first housing to supply power to the electronics circuit; and
(d) detecting physiological signals from the subject via the sensors.

30. The method as claimed in claim 29, wherein the monitoring device further includes an internal processor, the method further comprising processing the physiological signals in the internal processor.

31. The method as claimed in claim 29, wherein the monitoring device further includes a transmitter, the method further comprising transmitting data from the monitoring device to a remote device.

32. The method as claimed in claim 29, wherein the monitoring device further includes a transmitter and the physiological signals include a cardiac physiological signal, the method further comprising identifying a pulse event in the cardiac physiological signal and transmitting a marker indicating the occurrence of each pulse event to a remote device.

33. The method as claimed in claim 29, wherein the monitoring device further includes a memory unit, the method further comprising storing at least a portion of the physiological signals in the memory unit.

34. A monitoring device, comprising:
a lanyard;
a power source disposed on the lanyard;
one or more physiological sensors attached to the lanyard; and
an electronics package removably connectable to the lanyard, whereby power is supplied from the power source to the electronics package when the electronics package is connected to the lanyard and removal of the electronics package from the lanyard disconnects the electronics package from the power source.

* * * * *

UNITED STATES PATENT AND TRADEMARK OFFICE
CERTIFICATE OF CORRECTION

PATENT NO. : 7,257,438 B2 Page 1 of 1
APPLICATION NO. : 10/341833
DATED : August 14, 2007
INVENTOR(S) : Eric Kinast It is certified that error appears in the above-identified patent and that said Letters Patent is hereby corrected as shown below:

Column 1, line 6, "applications" should read --application--.
Column 1, line 7, "10/201075" should read --10/201,075--.
Column 5, line 15, "fact" should read --face--.
Column 5, line 23, delete "," after "common".
Column 18, line 2, "electronics" should read --electronic--.

Signed and Sealed this

Eighth Day of July, 2008

JON W. DUDAS
*Director of the United States Patent and Trademark Office*